US00PP27592P3

(12) United States Plant Patent
Travers

(10) Patent No.: US PP27,592 P3
(45) Date of Patent: Jan. 24, 2017

(54) ***CLEMATIS* PLANT NAMED 'TRA27'**

(50) Latin Name: ***Clematis* hybrid**
Varietal Denomination: TRA27

(71) Applicant: Bernard Travers, Saint Cyr en Val (FR)

(72) Inventor: Bernard Travers, Saint Cyr en Val (FR)

( * ) Notice: Subject to any disclaimer, the term of this patent is extended or adjusted under 35 U.S.C. 154(b) by 88 days.

(21) Appl. No.: 14/544,075

(22) Filed: Nov. 24, 2014

(65) Prior Publication Data

US 2016/0150705 P1 May 26, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Retrieved from the Internet on Apr. 18, 2016; http://www.newplantandflowers.com/clematis-with-exceptional-flowering-period/ "*Clematis* with exceptional flowering period," Feb. 7, 2013 (2 pgs total).*

UPOV—International Union for the Protection of New Varieties of Plants, PLUTO:Plant Variety Database; Apr. 14, 2016; citation for 'TRA27' (1 pg total).*

* cited by examiner

*Primary Examiner* — Susan McCormick Ewoldt
(74) *Attorney, Agent, or Firm* — Cassandra Bright

(57) ABSTRACT

A new and distinct *Clematis* hybrid named 'TRA27' is disclosed, characterized by unique pale violet-blue flowers. Flowers occur from the base of the plant to the top. Flowering season is continuous from April until September. The new cultivar is a *Clematis* typically suited for ornamental container and landscape use.

2 Drawing Sheets

Figure 1:
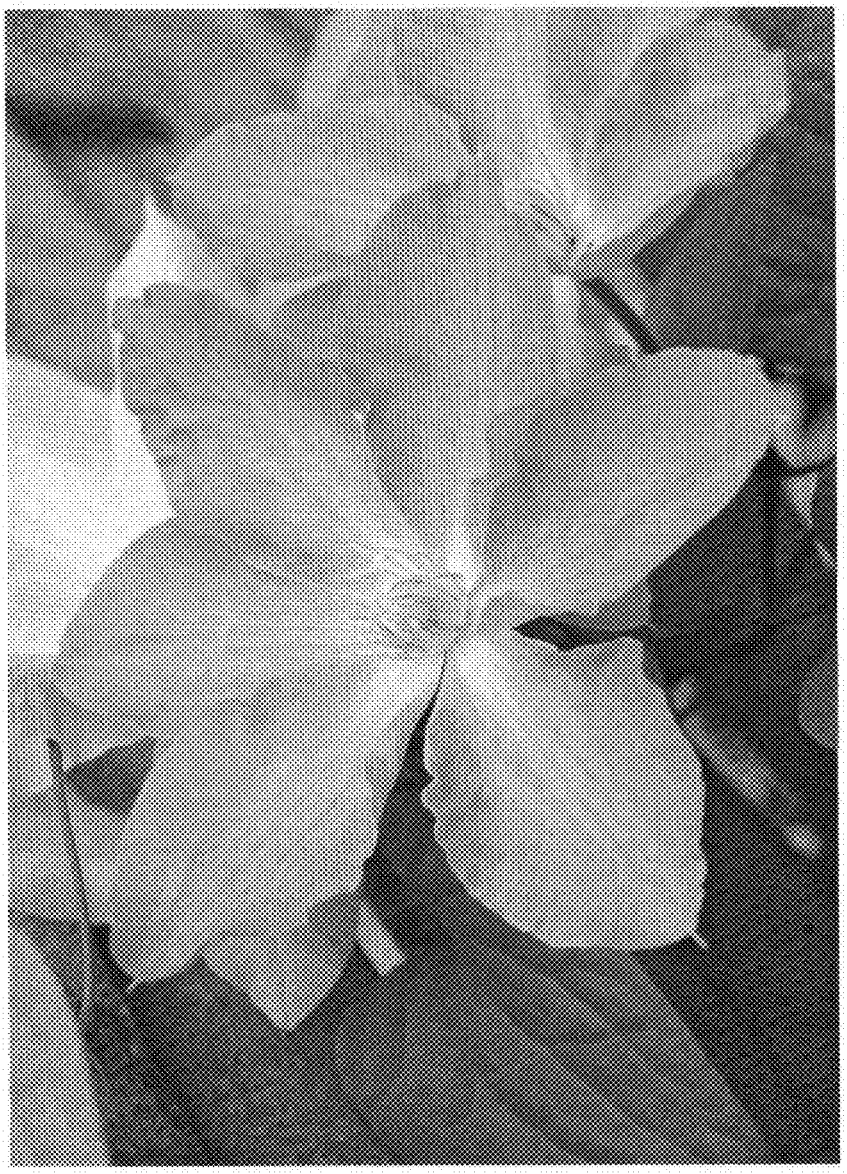

Latin name of the genus and species: *Clematis* hybrid.
Variety denomination: 'TRA27'.

BACKGROUND OF THE INVENTION

The new cultivar is the result of a breeding program, with the objective to develop new varieties of *Clematis* with strong growth and interesting flowers for commercial purposes. The new variety was discovered as a single plant among a group of seedlings of unknown parentage observed by the inventor, Bernard Travers. The discovery was made during 2002. Discovery was made at a commercial nursery in Orleans, France.

After selecting and isolating the new cultivar, asexual reproduction of the new cultivar 'TRA27' was first performed at a commercial nursery in St. Jean Le Blanc by vegetative cuttings during 2002. The inventor maintained the original plant, and observed the clones for several years, to establish stability of the characteristics. 'TRA27' has since produced multiple generations and has shown that the unique features of this cultivar are stable and reproduced true to type. Public access to plant material first occurred during early Spring of 2014. Before this time, plant material was under the control of the inventor, or those directly authorized by the inventor and no enabling access to plant material occurred. This variety has been applied for Plant Breeder's Right's Protection in the EU, with CPVO application number 2013/1735. A copy of the technical questionnaire is included with the mailing of this application. A grant has not yet issued, and technical exam process has not been completed. Neither this application, nor any other publication resulted in an enabling disclosure of 'TRA27'.

SUMMARY OF THE INVENTION

The cultivar 'TRA27' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TRA27'. These characteristics in combination distinguish 'TRA27' as a new and distinct *Clematis* cultivar:

1. Flowers occurring from base to top of plant
2. Many axillary flowers buds
3. Very pale violet-blue flowers
4. Yellow stamens
5. Long flowering season, with new flowers forming from Spring through Summer

PARENTAL COMPARISON

Parent varieties are unknown, the breeder is unable to supply records of the crossings.

COMMERCIAL COMPARISON

Plants of the new cultivar 'TRA27' can be compared to the known commercial variety *Clematis* hybrid 'HF Young' unpatented. The *Clematis* varieties are similar in most horticultural characteristics, however 'TRA27' differs from 'HF Young' in the following:

1. 'TRA27' has pale blue flowers, compared to violet flowers of comparator.
2. 'TRA27' has creamy yellow stamens and anthers. 'HF Young' has white stamens with white anthers.
3. 'TRA27' produces many flower buds at the axils, whereas this comparator produces a small amount of axillary flower buds.
4. 'TRA27' has elliptic tepals, whereas tepals of 'HF Young' are lanceolate.

Plants of the new cultivar 'TRA27' can be compared to the known commercial variety *Clematis* 'General Sikorsky', unpatented. The *Clematis* varieties have similar flower color and produce similar amounts of tepals. 'TRA27' differs from the comparator in the following:

1. Plants of 'TRA27' are much shorter and have more controlled growth.
2. 'TRA27' produces many axillary flower buds, whereas this comparator does not.
3. 'TRA27' produces a slightly smaller flower.
4. This comparator produces a flower with a somewhat red-purple center bar not found on flowers of 'TRA27'.
5. Stamens of the new variety are creamy yellow, whereas stamens of this comparator are yellow.

BRIEF DESCRIPTION OF THE PHOTOGRAPHS

The accompanying photograph in FIG. 1 illustrates in full color a typical flowers and foliage of 'TRA27'.

Figure 2:
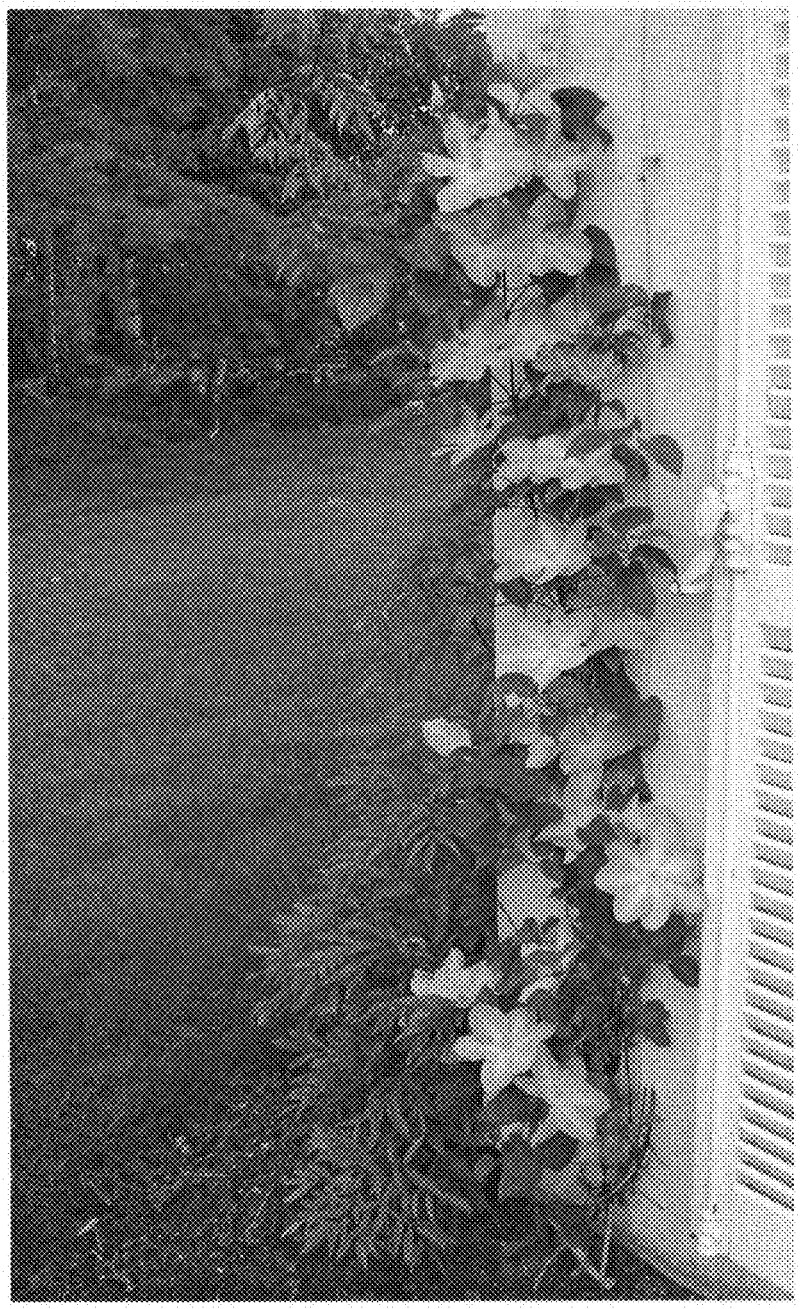

FIG. 2 depicts a plant of approximately 8 months, growing upright, and flowering all along the growth.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'TRA27' plants grown outdoors in Saint Cyr en Val, France. The growing temperature ranged from approximately −2° C. to 25° C. at night to 8° C. to 33° C. during the day. No artificial light, photoperiodic treatments or chemical treatments were given to the plants. Measurements and numerical values represent averages of typical flowering types.

Botanical classification: *Clematis* hybrid 'TRA27'.

Age of the plant described: Approximately 8 months.

PROPAGATION

Typical method: Vegetative cuttings.

Time to initiate rooting: Approximately 20 days at 21° C. or higher.

Time to produce a rooted plantlet: Approximately 40 days at 20° C. or higher.

Root description: Fine, fibrous.

PLANT

Growth habit: Climbing vine.

Height: Approximately 180 cm.

Plant spread: Approximately 50 cm.

Growth rate: Moderate. During active growing season in Spring, approximately 50 cm per month.

Branching characteristics: One main stem.

Length of main stem: Approximately 180 cm.

Diameter of main stem: Approximately 0.2 to 0.5 cm.

Main stem color: Near RHS Greyed-Purple 187A.

Main stem texture: Glabrous.

Internode length: Approximate range 5 cm to 11 cm.

Strength: Strong, flexible, semi-woody.

FOLIAGE

*Arrangement*.—Opposite, mostly single, occasionally compound trifoliate.

*Overall leaf length*.—Average 6.8 cm.

*Overall leaf diameter*.—Average 4.2 cm.

*Shape of blade*.—Ellliptic.

*Apex*.—Acute, occasionally short apiculate.

*Base*.—Cordate.

*Attachment*.—Stalked.

*Margin*.—Entire, slightly ciliate.

*Texture of both surfaces*.—Glabrous, leathery.

*Color*.—Young foliage upper side: Near RHS Green 143B. Young foliage under side: Near RHS Green 137C. Mature foliage upper side: Near RHS Green 137C. Very thin, fine margin near Greyed-Purple 183A. Mature foliage under side: Near RHS Green 137C. Very thin, fine margin near Greyed-Purple 183A.

*Venation*.—Type: Pinnate. Venation color upper side: Near RHS Green 143C. Venation color under side: Near RHS Green 143B.

Petiole:

*Length*.—Average range 2.0 to 4.0 cm.

*Diameter*.—Approximately 0.2 cm.

*Texture*.—Smooth.

*Color*.—Near RHS Greyed-Purple N186C.

FLOWER

Bloom period:

*Natural season*.—Continuous flowering April through September.

Inflorescence type and habit: Axillary occurring; 1 or 3; flowers facing outward.

Rate of flower opening: Approximately 7 days from bud to fully opened flower.

Flower longevity on plant: Approximately 8 to 12 days, after fully opened. Self-cleaning.

Flower fragrance: None.

Inflorescence size:

*Diameter*.—Average 11 to 15 cm.

*Depth*.—Average 6.0 cm.

Corolla:

*Tepal arrangement*.—Single whorl, overlapping.

*Quantity*.—6 per flower.

*Shape*.—Elliptic.

*Margin*.—Very slightly crenate, moderate undulation.

*Apex*.—Acute.

*Base*.—Truncate.

*Texture*.—Smooth, velvety.

*Length*.—Average Range 5.0 to 7.0 cm.

*Width*.—Average 3.1 cm.

Color:

*Tepals*.—When opening: Upper surface: Near RHS Violet-Blue 97B with median line near Violet-Blue 97D. Lower surface: Near RHS Violet-Blue 98C with streaks near Violet-Blue 97D. Fully opened: Upper surface: Near RHS Violet-Blue 97C with median line near Violet-Blue 97D. Lower surface: Near RHS Violet-Blue 97C with streaks near Violet-Blue 97D. Ageing: Upper surface: Near RHS Violet-Blue 97C with center streaks near Violet-Blue 97D. Lower surface: Near RHS Violet-Blue 97C with streaks near Violet-Blue 97D.

Bud:

*Shape*.—Elongated sphere.
*Length*.—Approximately 12 cm.
*Diameter*.—Approximately 6.7 cm.
*Color*.—Near RHS Violet-Blue 97A.

Pedicels:

*Length*.—Average range 6 to 12 cm.
*Width*.—Approximately 0.4 cm.
*Angle*.—Average 45° to 80°.
*Strength*.—Flexible.
*Color*.—Near RHS Green 137A heavily flushed Purple N79A.

REPRODUCTIVE ORGANS

Stamens:

*Number*.—Average 80 per flower.
*Anther length*.—Approximately 0.4 cm.
*Anther color*.—Near RHS Yellow-White 158A.
*Anther shape*.—Oblong.
*Filament length*.—Approximately 1.4.
*Filament color*.—Near RHS Yellow-White 158C.
*Pollen quantity*.—Moderate.
*Pollen color*.—Greyed-Yellow 161D.

Pistil:

*Length*.—Approximately 2.5 cm.
*Style length*.—Approximately 1.1 cm.
*Stigma*.—Shape: Fine irregular hairs. Color: Near RHS Green-White 157B.

OTHER CHARACTERISTICS

Seeds: Seed production not observed.

Disease/pest resistance: Neither resistance nor susceptibility to normal diseases and pests of *Clematis* has been observed.

Temperature tolerance: Tolerates temperatures from approximately −20° C. to 45° C.

What is claimed is:

1. A new and distinct cultivar of *Clematis* hybrid plant named 'TRA27' as herein illustrated and described.

* * * * *